(12) United States Patent
Johansson

(10) Patent No.: US 6,755,820 B1
(45) Date of Patent: Jun. 29, 2004

(54) LASER PROBE FOR MEDICAL TREATMENT

(76) Inventor: Susanne Johansson, Ringvägen 10, Stockholm (SE), SE-117 26

( * ) Notice: Subject to any disclaimer, the term of this patent is extended or adjusted under 35 U.S.C. 154(b) by 0 days.

(21) Appl. No.: 10/088,809

(22) PCT Filed: Sep. 19, 2000

(86) PCT No.: PCT/SE00/01812

§ 371 (c)(1),
(2), (4) Date: May 30, 2002

(87) PCT Pub. No.: WO01/21256

PCT Pub. Date: Mar. 29, 2001

(30) Foreign Application Priority Data

Sep. 20, 1999 (SE) .............................................. 9903393

(51) Int. Cl.[7] .............................................. A61B 18/20
(52) U.S. Cl. ................................ 606/13; 606/3; 607/89
(58) Field of Search ........................ 606/9, 13; 607/88, 607/89

(56) References Cited

U.S. PATENT DOCUMENTS 5,824,023 A * 10/1998 Anderson .................... 607/88
6,187,029 B1 * 2/2001 Shapiro et al. ............... 607/88
6,312,451 B1 * 11/2001 Streeter ....................... 607/89
6,443,978 B1 * 9/2002 Zharov ........................ 607/91

FOREIGN PATENT DOCUMENTS

WO    WO 90/00420    * 1/1990    ............ A61N/5/06

OTHER PUBLICATIONS

Patent Abstracts of Japan, JP 096018A, Apr. 20, 1993.

* cited by examiner

Primary Examiner—Linda C. M. Dvorak
Assistant Examiner—H M. Johnson
(74) Attorney, Agent, or Firm—Ware, Fressola, Van der Sluys & Adolphson LLP

(57) ABSTRACT

In a probe (10, 20) for laser treatment of uneven structures or deformations of a body, the laser devices (16, 20, 22) are arranged on a partially domed surface (18, 24) in order to cover the uneven structures. The doming has a smooth surface treatment, which facilitates sweeping in the probe over uneven structures. The probe includes a handgrip (12), covered with a material that increases the adhesion to a hand. In particular, the probe is intended for treatment of neurological and rheumatic disease conditions.

11 Claims, 2 Drawing Sheets

LASER PROBE FOR MEDICAL TREATMENT

BACKGROUND OF THE INVENTION

1. Technical Field

The present invention relates to a probe to be used for laser treatment of preferably neurological and rheumatic diseases or for preventative purposes.

2. Description of the Background Art

The use of lasers within science and medicine for the treatment of diseases and in therapy is currently widespread. Many researchers and research groups are performing experiments concerning tissue reactions in vitro in order to survey, predict and explain the effects of laser irradiation. Other researchers carry out tests in vivo on animals. Clinical research and clinical treatment have also been documented.

One of the persons who leads research in the field is Semion Rochkind, previously Chairman of the "World Association for Laser Therapy". Rochkind's profession is as a neurosurgeon at the Department of Neurosurgery, Tel Aviv, Sourasky Medical Center, Israel. He has studied laser therapy in relationship to peripheral nerves and spinal injuries since 1978.

The laser probes that are used for the treatment of patients have a plane treatment surface, which means that uneven parts and deformations on a body, when the probe is swept over them, create undesirable spaces between the body and the laser devices that exist on the [probe] surface. In order for an effective treatment to be achieved, the therapist who performs the treatment must know the exact light dose that is to be applied at various places of a body during treatment. Over- or underexposure, for example, means that the principally desired healing takes place in tissues or organs where it is not desired.

A therapist who performs treatment has many years of experience and must know where to apply radiation to tissue and how much to apply, for example, with respect to the power of the laser measured in mW, and which wavelength of light is most suitable for different types of treatment.

Thus, today's laser probes constitute a problem when treating uneven parts of the body, that is, parts of the body that do not have only even skin.

Furthermore, known laser probes are slippery to hold, which is why the sweeping of a probe over a body surface, particularly one such as the spine with uneven parts, results in the one who is sweeping the probe easily slipping or in some other way losing his or her grip, leading to erroneous dosage of the light or other drawbacks. Furthermore, gels are often used to obtain better contact between the skin and the probe, and these are messy. Therapists and other health-care personnel often apply various salves to their hands in order to prevent drying of the skin, and this also introduces a risk for slipping when the probe is being swept. Laser probes are expensive instruments and will not survive, for example, being dropped on the floor. Thus it is important to obtain a more secure handgrip for the probe.

A laser probe is previously known from patent application JP 5-96018. The probe has the shape of a cup and is attached to the female breast with the aid of vacuum suction in order to stimulate the production of breast milk. Thus, it cannot be swept over a body, in particular a spine, and thus does not in any way solve the problems that the present invention solves. A cup-shaped probe cannot be continuously swept over, for example, a spine. Nor does the patent application state how closely the probe should be in contact with a part of the body. On the contrary, the attached drawing shows that the laser diodes that are used do not contact tightly against the part of the body, in this case a breast.

The probe according to the present invention is defined in more detail in the attached independent claims. Further embodiments of the probe are specified in the attached non-independent claims.

SUMMARY OF THE PRESENT INVENTION

The invention concerns a probe to be used for laser treatment of body tissue. In one aspect of the invention the problem concerning the treatment area of the probe is solved such that it can be used on uneven parts of a body, such as the human spine.

Another aspect of the invention comprises that it will be possible to sweep the probe held by a hand along a pathway with uneven sections in a smooth manner in order to facilitate adequate treatment and minimize the risk that the probe is dropped.

A further aspect of the invention makes possible treatment of a body structure with the probe in one coherent motion.

In order to solve problems associated with instruments for laser treatment, a probe with a handgrip is specified in the present invention for laser treatment of uneven parts or deformations of a body. It has a surface that lies against the body during treatment. Furthermore, the surface comprises laser devices. The surface according to the invention is at least partially domed from one of its side edges to another of its side edges or along a diagonal line in order to be able to surround as tightly as possible the said uneven parts or deformations when the probe is in use and swept over a body.

If the contact surface of the probe is circular, the doming preferentially stretches over its diameter.

In one embodiment of the invention at least one laser device is included in the doming.

A further embodiment of the invention comprises the doming having a smooth surface treatment, which facilitates the sweeping of the probe along a body structure.

A further embodiment of the invention specifies that the doming is elastically designed so that it yields to a certain extent when touched or changes its form according to the body structure that it is swept along when the probe is in use.

In a further embodiment of the present invention the probe comprises a device for adjustment of the domed surface such that it becomes possible to adapt it to different structures on a body.

A further embodiment of the present invention comprises the handgrip being coated with a material that increases its adhesiveness to a hand, whereby the probe cannot deviate so easily from the direction in which it is intended that it should move during contact.

BRIEF DESCRIPTION OF THE DRAWINGS

Henceforward in the description, reference will be made to the attached drawings in order to better understand the invention and its embodiments, whereby.

DETAILED DESCRIPTION OF PREFERRED EMBODIMENTS

Figure 1:
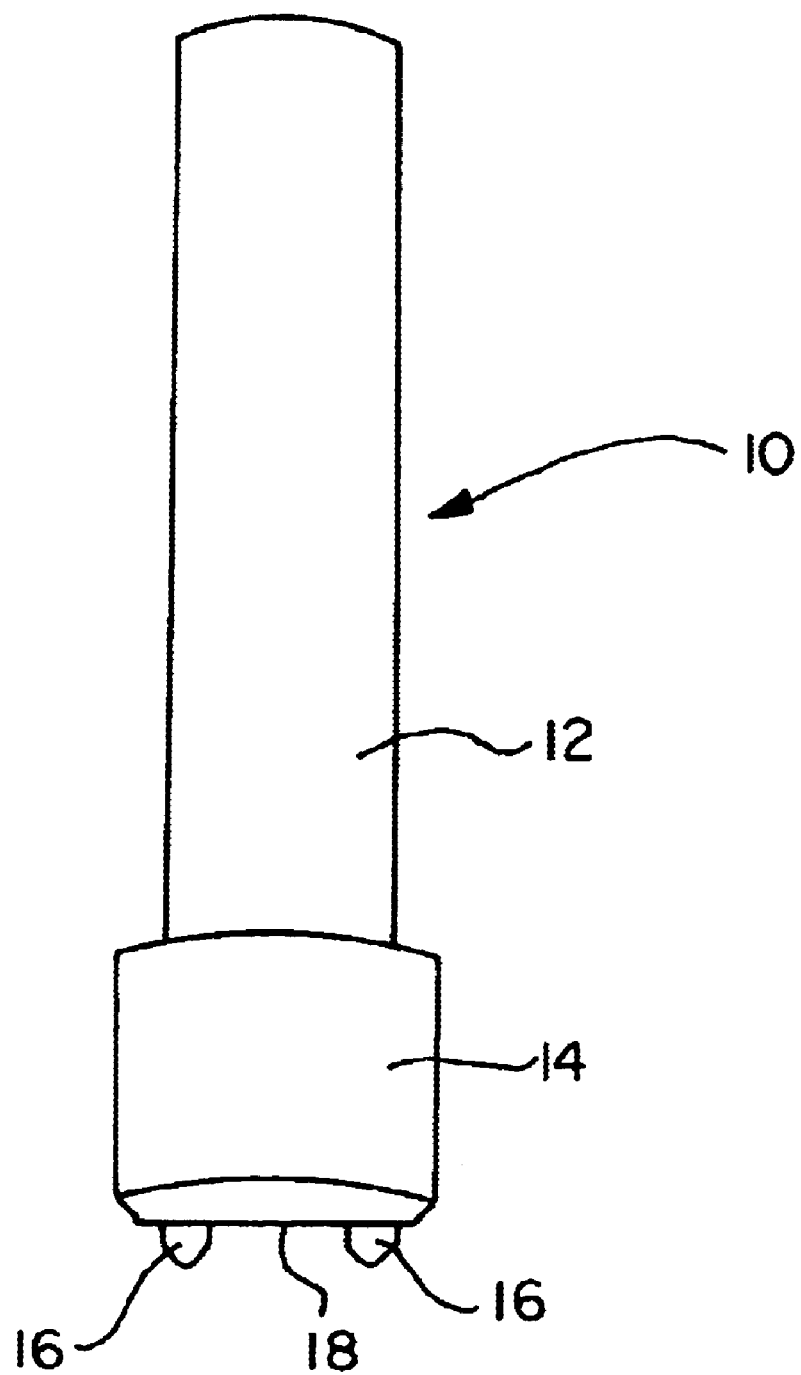
FIG. 1 is a side view of a laser probe according to the prior art.

The invention according to the present description specifies a laser probe, that when in use is used to treat bodily ailments (animals are not excluded). Such a probe can be used both for the treatment of diseases and for preventative purposes.

Henceforth, the invention, in the form of the probe and its embodiments will be described as a probe designed for treatment of a spine as a body structure, but the present invention is not for that reason limited only to be suitable for the spine, and other uneven body structures or deformations can be considered for treatment by the probe.

The present invention is not directed towards a treatment of various disease conditions, but it is directed towards an instrument in the form of a laser probe that can be used during such treatment.

Treatment of nerve cells with laser therapy will not be discussed in more detail here, and the reader is referred to scientific studies and similar, such as "Isolated Neuron Response to Blue Laser Microirradiation: Phenomenology and Possible Mechanism", A. B. Uzdensky, Department of Biophysics and Biocybernetics, Physical Faculty, Rostov State University, Stachky av., 194/1, Rostov-on-Don. 344090, Russia and Rochkind S. (1992) "Spinal Cord and Brain transplantation benefited by low-power laser irradiation". Lasers in Medical Science 7: 143–115, etc.

However, a brief description of how a patient with multiple sclerosis (MS) may be treated follows.

The patient's medical history is recorded, whereby it is important to determine how a disease has commenced. This is related to the fact that the first healing effects of a treatment always arise in that area of the body that was last attacked by the disease.

A first stage of a treatment, in this case of MS, is to treat the spine. The region between vertebrae C1–C7 is treated with 2,500 mW for 5 minutes. Thereafter the region from C1 to the sacrum is treated with 5,000 mW for 5 minutes, and a further 5 minutes from C1 to the sacrum with 2,500 mW. The patient thereafter lies on his or her back for treatment of the frontal lobe from temple to temple with 5,000 mW for 4 minutes. Great care is required in this operation to prevent the light from the laser probe reaching the eyes. Care is taken to ensure that the patient's eyes are closed during the treatment.

If a patient has reduced mobility in the legs, the feet should also be treated to stimulate blood circulation, whereby 5,000 mW is applied for 5 minutes to each foot. It is important to be careful that treatment of the feet does not continue for too long so that too much of the energy is transferred to the feet, whereby the principal healing is not achieved in the spine or frontal lobe.

After the laser treatment, a patient can feel heat as a burning sensation accompanied by tingling, which is often described as light pin-pricks or prickling in the arms and legs. These treatment effects can move around in the body, whereby most reactions arise in the area of the spine.

A treatment takes approximately 30 minutes. The first ten treatments should be carried out at a frequency of two times per week. Noticeable results of the treatment arise after approximately 8–10 treatments.

It has been shown that patients follow the same pattern of experiences, independent of age, gender or degree of advancement of their disease. After completion of treatment, a patient can feel active with a pleasant feeling of warmth in the body, or a tiredness with a feeling of muscular pains.

One permanent or long-term effect of the treatment against MS is that patients have achieved a noticeable improvement in movement and breathing organs together with an increase in general energy.

A probe 10 for laser treatment or therapy according to the prior art is shown in FIG. 1.

The probe has a handgrip 12 and a foot 14 comprising laser devices 16, such as laser diodes or similar. The laser devices 16 are comprised per se in a bottom surface or treatment surface 18 of the foot 14. The surface 18 comprises also a number of normal light devices such as LEDs (light-emitting diodes, not shown) in order to warn that laser treatment is being performed.

The probe 10 according to FIG. 1 has a smooth surface 18 that makes difficult an even treatment of body structures such as the spine, with the risk of overstimulation or overexposure of a treated area of a body.

Furthermore, the probe 10 according to FIG. 1 has a smooth handgrip 12, which makes the sweeping of the probe over uneven body structures difficult, resulting in slipping or twisting, and also the risk of the probe 10 being dropped onto, for example, a floor. It can also be appreciated that the smooth treatment area 18 means that the probe 10 can make contact with, for example, a vertebra with the result that the probe is dropped or other difficulties arise.

Probes according to FIG. 1 and the below-described probe of the present invention have electronic circuits that are connected to control devices (not shown) for the probe. The control devices and other electronic circuits consist of known technology and do not form part of the present invention, which is why they will not be described in detail in the following.

Figure 2A:
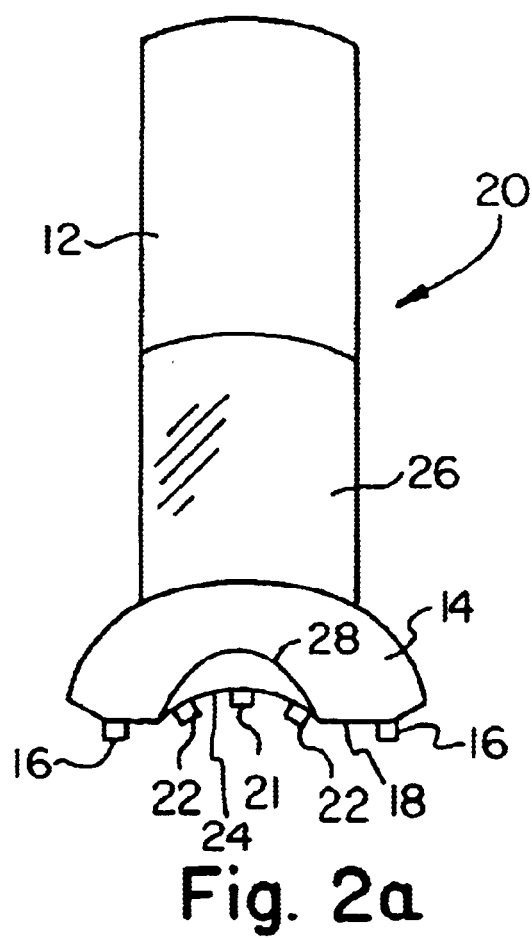
FIG. 2a is a side view of a laser probe according to the present invention.

In order to solve the problems with the probe 10 according to the prior art, the present invention specifies a probe 20 according to FIG. 2a. The probe 20 has a handgrip 12 and a foot 14 comprising laser devices 16 and light-emitting diodes 22 as described above. The probe 20 thus far agrees with the probe 10 according to FIG. 1. In order to solve the said and other problems with probes 10 or similar, the foot 14 has been equipped with a domed surface 24 and with a rubber surface 26 or other device (such as a knurling) that increases adhesion to a hand. The domed surface 24 is of such a form that it is adapted in the best possible way to the area of the body on which it is intended to be used for laser treatment. The doming 24 can also be flexible in its embodiment, that is: it can be made from some known material that is elastic or resilient, but which can even then hold laser devices and light devices. The resilient or flexible property of the material used has been specified with a dotted line 28 in FIG. 2a. One potential material is some spring steel with an elasticity that is suitable for the purpose. The material used is preferably surface-treated with a suitable known material to achieve a smooth surface and a surface that does not harm the body part that is being treated, that is, it also achieves comfort for a patient during treatment.

The doming 24 can also be achieved with the aid of some screw device (for example, adjustment screws, not shown) attached from above in the domed surface, whereby the doming can be adjusted as required. The screw device can also be connected to a servo-motor for machine adjustment (not shown).

Furthermore, the doming 24 stretches from edge to edge or along a diagonal, diameter, chord, etc., depending on the design of the foot 14.

A further embodiment of the present invention specifies that a laser device 21 has been placed inside the doming 24, which means that treatment of, for example, the spine can be performed in a symmetrical manner.

With a treatment probe 20 according to the present invention, more efficient and shorter treatment of patients is achieved, primarily with respect to patients with neurological and rheumatic diseases. Not only is a reduced treatment time for a patient achieved with the accompanying reduction in the risk of overstimulation and overexposure resulting in the loss of the treatment effect, but also the conditions for a therapist are improved since the design of the probe 20 makes it possible to focus on the area that is being treated. The actual handling of a probe is corrected and made simpler in that two treatment stages are reduced to one as described in the following, with reference to FIG. 2*b*.

Figure 2B:
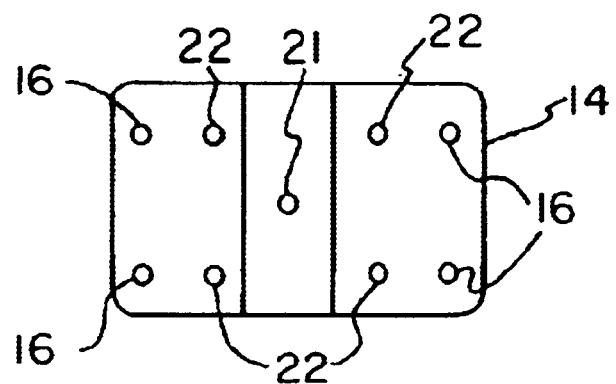
FIG. 2b is a bottom view of the laser probe of the present invention.

FIG. 2*b* shows the foot 14 of the probe viewed from beneath so that the treatment surface appears, whereby the doming 24 between the solid cross-lines is made clear. The treatment surface can in one embodiment be rectangular, for example 4.0×3.5 cm, and slightly concave (domed 24), that is: it can be adapted to, for example, the spine, and comprise five laser devices 16, 21. Two of the laser devices 16 are arranged along each short/long side of the doming 24, and one of the laser devices 21 is arranged in the center of the doming 24. With this arrangement and embodiments all treatment areas are reached simultaneously, whereby what is known as the output power of the treatment becomes better and the reaction of a patient to the treatment can be determined even while the treatment is being performed. This makes it possible for the first time in the field of laser treatment to accommodate, design and modify the treatment in real-time with respect to both content and time, following the pattern of reaction of an individual patient, during the actual treatment session.

The present invention is not limited to the examples or embodiments described here. It is rather the extent of the attached claims that specify the scope of protection for one skilled in the arts in the technical field.

What is claimed is:

1. Probe for laser treatment of uneven structures or deformations of a body, the probe comprising:

(a) a handgrip;

(b) one surface adjacent the handgrip and designed to make contact with the body during treatment, the surface is at least partially domed from one side edge to another side edge, along a direction chosen from the group consisting of a diagonal, diameter and chord, in order to be able to surround as tightly as possible the uneven structures or deformation when the probe in used and swept over a body, whereby an entire treated area can be simultaneously covered;

(c) adjustment devices having the doming connected thereto; and (d) laser devices included in the surface.

2. Probe according to claim 1, wherein at least one of the laser devices is included in the doming.

3. Probe according to claim 2, wherein the doming has a smooth surface treatment, which facilitates sweeping of the probe.

4. Probe according to claim 3, wherein the doming is elastically designed to yield somewhat upon contact.

5. Probe according to claim 4, wherein the handgrip is covered with a material that increases adhesion to a hand, whereby the probe cannot so easily deviate from an intended direction of motion during contact.

6. Probe according to claim 1, wherein the doming has a smooth surface treatment, which facilitates sweeping of the probe.

7. Probe according to claim 6, wherein the doming is elastically designed to yield somewhat upon contact.

8. Probe according to claim 7, wherein the handgrip is covered with a material that increases adhesion to a hand, whereby the probe cannot so easily deviate from an intended direction of motion during contact.

9. Probe according to claim 1, wherein the doming is elastically designed to yield somewhat upon contact.

10. Probe according to claim 9, wherein the handgrip is covered with a material that increases adhesion to a hand, whereby the probe cannot so easily deviate from an intended direction of motion during contact.

11. Probe according to claim 1, wherein the handgrip is covered with a material that increases adhesion to a hand, whereby the probe cannot so easily deviate from an intended direction of motion during contact.

* * * * *

UNITED STATES PATENT AND TRADEMARK OFFICE
CERTIFICATE OF CORRECTION

PATENT NO. : 6,755,820 B1
DATED : June 29, 2004
INVENTOR(S) : Susanne Johansson

It is certified that error appears in the above-identified patent and that said Letters Patent is hereby corrected as shown below:

Column 3,
Line 27, "115" should be -- 151 --.

Column 6,
Line 5, "in" should be -- is --.

Signed and Sealed this

Seventh Day of September, 2004

JON W. DUDAS
*Director of the United States Patent and Trademark Office*